United States Patent [19]

Jing

[11] Patent Number: 5,407,831
[45] Date of Patent: Apr. 18, 1995

[54] METHOD FOR EXTRACTING ELEMENTS SUCH AS LEAD IN BLOOD

[75] Inventor: Jung Jing, Columbus, Ohio

[73] Assignee: The Ohio State University Research Foundation, Columbus, Ohio

[21] Appl. No.: 72,598

[22] Filed: Jun. 3, 1993

[51] Int. Cl.$^6$ .................. G01N 30/00; G01N 33/50
[52] U.S. Cl. .................................. 436/74; 436/73; 436/177; 436/178
[58] Field of Search .................. 436/74, 73, 177, 178

[56] References Cited

U.S. PATENT DOCUMENTS

| | | |
|---|---|---|
| 4,028,130 | 6/1977 | Webster et al. |
| 4,403,039 | 9/1983 | Ban et al. ........................ 436/150 |
| 4,832,847 | 5/1989 | Fujii et al. ........................ 210/616 |
| 5,039,618 | 8/1991 | Stone .............................. 436/77 |
| 5,055,402 | 10/1991 | Greene et al. .................... 435/174 |
| 5,094,944 | 3/1992 | Hayes ............................. 435/29 |
| 5,149,656 | 9/1992 | Bitton et al. ..................... 435/288 |
| 5,193,936 | 3/1993 | Pal et al. ......................... 405/128 |

OTHER PUBLICATIONS

Abstract, "Cadmium Uptake by Plants and its Correlation With Sewage Sludge CD Extractability," by Dr. Jung Jing, Feb. 1990.
"Contribution of Social and Developmental Factors to Lead Exposure During the First Year of Life," *Pediatrics*, by Kim N. Dietrich et al., vol. 75, No. 6, Jun. 1985, pp. 1114–1119.
"Assessing the Contribution From Lead in Mining Wastes to Blood Lead," *Regulatory Toxicology and Pharmacology*, by Martha J. Steele et al., 1990, pp. 158–190.
"Bioavailability of Arsenic and Lead in Soils from the Butte, Montana, Mining District," *Environ. Sci. Technol.*, by Andy Davis et al., vol. 26, No. 3, 1992, pp. 461–468.
"Lead Bioavailability: Dissolution Kinetics Under Simulated Gastric Conditions," *Environ. Sci. Technol.*, by Michael V. Ruby et al., vol. 26, No. 6, pp. 1242–1248.
"Relative Bioavailability of Lead From Mining Waste Soil in Rats," *Fundamental and Applied Toxicology*, by G. B. Freeman et al., vol. 19, 1992, pp. 388–398.
"Estimation of Isotopically Exchangeable Cadmium and Zinc in Soils," by R. Fujii and R. B. Corey, *Soil Sci. Soc. Am. J.*, vol. 50, 1986.
"A Method for Controlling the Activities of Free Metal Hydrogen, and Phosphate Ions in Hydroponic Solutions Using Ion Exchange and Chelating Resins," by Checkai et al., *Plant and Soil 99*, 321–334, 1987.
"Chelating Resin Method for Estimation of Sludge—Cadmium Bioavailability," by J. Jing et al., *Commun. Soil Sci. Plant Anal.*, 22(19&20), 2029–2035 (1991).
"A Chelating–Resin Method for Characterizing Soluble Metal Complexes," by L. L. Hendrickson et al., *Soil Sci. Soc. Am. J.*, 47:467–474, 1983.
"Use of Chelating Resins in Metal Adsorption tudies," by M. A. Turner et al., *Soil Sci. Soc. Am. J.*, 48:763–769, 1984.
"Heavy Metals in the Environment, Effects of Sewage Sludge Cadmium Concentration on Chemical Extractability and Plant Uptake," by Jung Jing et al., *J. Environ. Qual.*, 21:73–81, 1992.
Abstract entitled "bioavailability of Cadmium in Municipal Sewage Sludge," vol. 51, No. 10, Apr. 1991, *Dissertation Abstracts International.*
Thesis entitled "Bioavailability of Cadmium in Municipal Sewage Sludge," by Jung Jing, The Ohio State University, 1990.

*Primary Examiner*—Jill A. Warden
*Attorney, Agent, or Firm*—Calfee Halter & Griswold

[57] ABSTRACT

A simple and sensitive method for extracting an inorganic element, including toxic metals such as lead or antimony or non-metallic elements such as arsenic, selenium or tellurium from animal blood, including human blood, is provided by the present invention. The sample of blood or portion of blood, such as red cells, is first mixed with an neutral salt solution. The mixture of cells and buffer is then exposed to a chelating resin which removes the inorganic element, such as lead, from solution. Thereafter, the resin is packed in a column and the element, such as lead, is eluted. The amount of eluted element, such as lead, is measured by conventional methods, such as atomic absorption spectrophotometry.

12 Claims, 1 Drawing Sheet

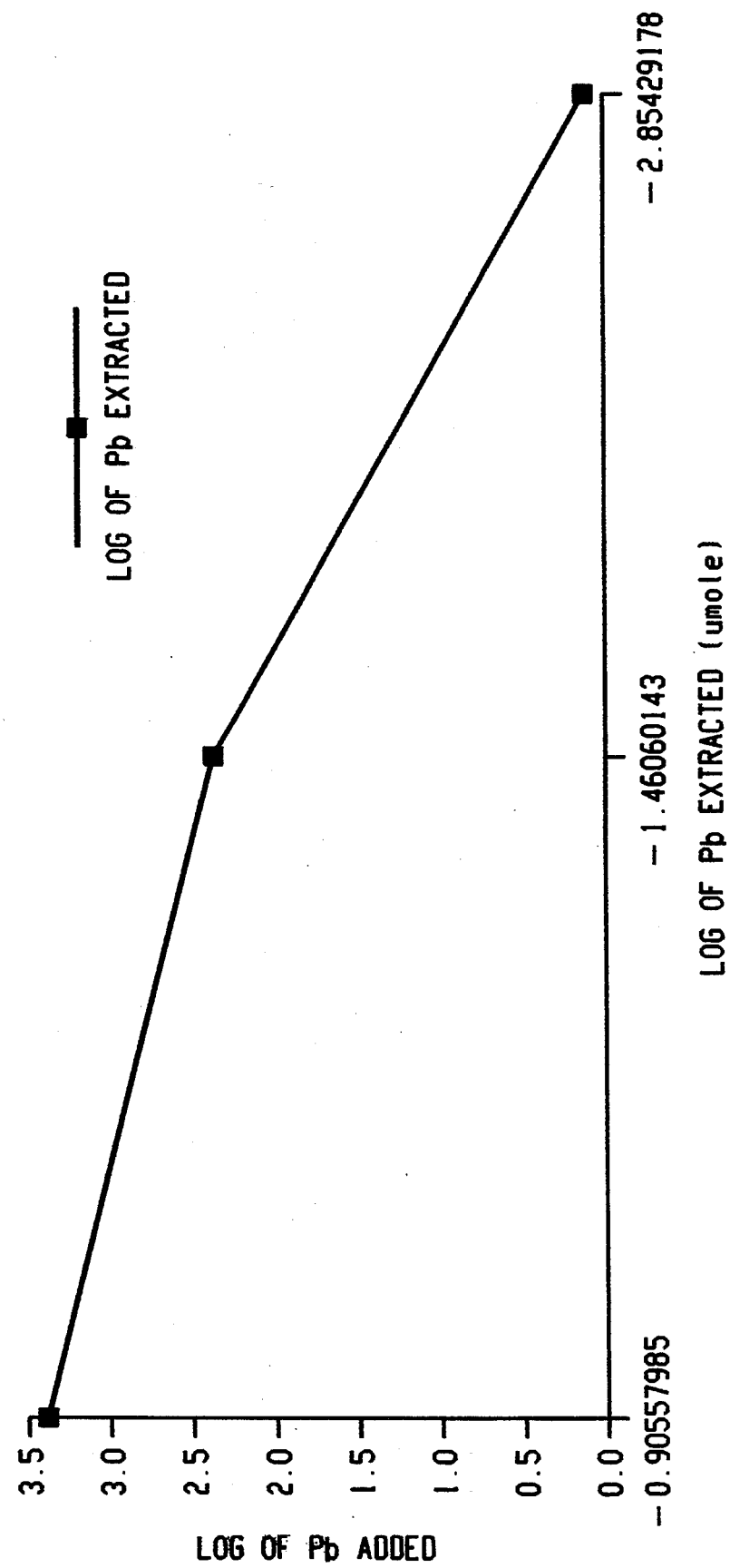

METHOD FOR EXTRACTING ELEMENTS SUCH AS LEAD IN BLOOD

BACKGROUND OF THE INVENTION

The accumulation of several toxic elements, such as lead, within human beings can cause significant, serious health problems. For example, the accumulation of lead within children can lead to a variety of behavioral and educational disabilities. To determine whether metal toxicity is the cause of such problems, it is desirable to have a simple and sensitive method for measuring the levels of an element in the blood or extracting an element, such as lead from blood. Such a method would also enable physicians to monitor the efficacy of treatments for reducing the deleterious accumulation of this metal in the body.

SUMMARY OF THE INVENTION

The present invention provides a simple and sensitive method for extracting inorganic elements, including toxic metals such as lead or antimony or non-metallic elements such as arsenic, selenium or tellurium from animal blood, including human blood. The sample of whole blood or portion of blood, such as red cells, is first mixed with an neutral salt solution. The mixture of cells and salt solution is then exposed to a chelating resin which removes the inorganic element, such as lead, from the mixture. Thereafter, the resin is packed in a column and the element, such as lead, is eluted. The amount of eluted element, such as lead, is measured by conventional methods, such as atomic absorption spectrophotometry.

Brief Description of the Drawings

FIG. 1 is a graph showing the log of lead added vs. the log of lead extracted and shows the relationship between the amount of lead added to a sample containing red blood cells and the amount of lead extracted the sample of red blood cells.

Detailed Description of the Invention

The present invention provides a method for extracting several inorganic elements, including toxic elements such as lead, from blood without disrupting the blood cells. The method can also be used to monitor over time the levels of lead and other elements such as arsenic, selenium, and tellurium in blood, including red blood cells.

Method of Extraction of Lead from Blood

The sample of blood, such as red blood cells, is combined with a neutral, that is having a pH of between about 6.5 and 7.5, salt solution containing 1 mM to 10M salt, preferably a nitrate, such as 0.05M $Ca(NO_3)_2$, preferably containing an agent to prevent microbial growth such as 2 g/L $NaN_3$. A semipermeable container, such as a bag made from dialysis tubing, containing a chelating resin is then added to the mixture of neutral salt solution and red blood cells. A suitable resin of this type is available under the trade name "Chelex 100" from Bio-Rad Laboratories. The salt solution, red blood cells, and bag of resin are then incubated for a sufficient time, such as 0.5 to 48 hours, to remove all or a portion of the element from the salt solution and red blood cells, preferably 25 hours, preferably at ambient temperature. At the end of the incubation period, the dialysis tubing is removed from the salt solution and preferably washed with deionized water to remove any red blood cells from the outside of the tubing. The dialysis tubing is then cut open and the enclosed salt solution and resin washed into a column made of a non-adherent and non-reactive material, such as glass, polycarbonate or polystyrene.

The initial salt solution that runs through the column is collected and passed through the column several times to ensure that all resin beads are transferred to the column. An additional wash, preferably 5 mL of deionized water, is used to elute any remaining neutral salt solution from the resin-packed column. This wash is discarded. The resin-packed column then is eluted with an elution solution, such as an 0.1 to 10.0M acid solution, preferably 0.5M $HNO_3$.

The element, such as lead, in the eluant is measured by conventional methods such as flame atomic absorption spectrophotometry (AA) or graphite furnace atomic absorption spectrophotometry (graphite).

EXAMPLES

Example 1

To determine the amount of lead which can be extracted by the method of this invention, the following procedure was used. A 100 mL sample of blood cells obtained from the American Red Cross Central Ohio Region, Columbus, Ohio, was mixed with a neutral salt solution, consisting of 0.05M $Ca(NO_3)_2$ and 2 g/L $NaN_3$. A dialysis bag containing 1 g of Chelex 100 resin was combined with the mixture of red cells and salt solution in a 250 ml Erlenmeyer flask. The flask was agitated on a horizontal shaker at 200 RPM for 25 hours at ambient temperature. A control sample containing a neutral salt solution but no red blood cells was also incubated with the chelating resin for 25 hours. The resin was transferred to a glass column and jet-washed into the column. Lead was eluted into 8 mL glass collection vials with 0.5M $HNO_3$. The 8 mL glass collection vials were prewashed with Micro (TM) solution, rinsed with deionized water three times, and oven dried at about 70° C. prior to collection of eluant. Approximately twelve aliquots of approximately five grams each of eluant were collected for a total of approximately 60 g.

The lead in each aliquot of eluant was measured by flame atomic absorption spectrophotometry (AA), using a Perkin Elmer 3030B atomic absorption spectrophotometer. The lead in selected vials was also measured by graphite furnace atomic absorption spectrophotometry (graphite). The instrument used in the analysis was a Varian-300 Zeeman graphite furnace atomic absorption spectrophotometer with the wavelength set at 283.3 nm. During the analysis the temperature was increased from 75° C. to 2500° C. and the eluant was exposed to argon gas at a flow rate of 3L/min. The graphite furnace spectrophotometer is preferred when levels of lead in the vial fall below 0.1 $\mu g/g$. The results of this analysis are shown in Table 1 and summarized in Table 3.

Comparative Example 1

To determine the portion of lead which can be extracted by the method of this invention when excess lead is added to blood, the following procedure was used. 200 $\mu g$ of lead in a lead nitrate, $Pb(NO_3)_2$, water solution was added to a mixture of red blood cells and neutral salt solution as described in example 1. All other steps in the analysis were identical to those described in example 1. This concentration of lead in blood, 200 μg/100 ml, is the lethal dosage for humans. The results of this analysis are shown in Table 1 and summarized in Table 3.

Comparative Example 2

To determine the portion of lead which can be extracted by the method of this invention when excess lead is added to blood, the following procedure was used. 2000 μg of lead in a lead nitrate, $Pb(NO_3)_2$, water solution was added to a mixture of red blood cells and neutral salt solution as described in example 1. All other steps in the analysis were identical to those described in example 1. The results of this analysis are shown in Table 1 and summarized in Table 3.

Comparative Example 3

To determine the recovery capacity of the chelating resin for lead from a salt solution alone, a sample containing 100 ml of neutral salt solution, consisting of 0.05M $Ca(NO_3)_2$ and 2 g/L $NAN_3$, and 10 μg lead in a lead nitrate $Pb(NO_3)_2$ water solution was prepared without red cells. All other steps in the analysis were identical to those described in example 1. The results of this analysis are shown in Table 2 and summarized in Table 3.

Comparative Example 4

To determine the recovery capacity of the chelating resin for lead from a salt solution alone, a sample containing 100 ml of neutral salt solution, consisting of 0.05M $Ca(NO_3)_2$ and 2 g/L $NAN_3$, and 100 μg lead in a lead nitrate $Pb(NO_3)_2$ water solution was prepared without red cells. All other steps in the analysis were identical to those described in example 1. The results of this analysis are shown in Table 2 and summarized in Table 3.

TABLE 1

Extraction of Lead from Red Cells

| Sample no. | Vial wt (g) | Vial & sample (g) | Pb (μg/g) AA | Pb (μg/g) graphite | Total Pb in each tube |
|---|---|---|---|---|---|
| 2000-1 | 9.63 | 14.99 | 4.636 | off scale | 24.84896* |
| 2000-2 | 9.79 | 16.53 | 0.054 | 0.093 | 0.62682 |
| 2000-3 | 9.63 | 14.59 | 0.022 | 0.002 | 0.0992 |
| 2000-4 | 9.79 | 14.94 | 0.009 | 0.011 | 0.0515 |
| 2000-5 | 9.69 | 14.72 | 0.026 | — | 0.1000* |
| 2000-6 | 9.65 | 14.73 | 0.004 | — | — |
| 2000-7 | 9.62 | 14.89 | 0.009 | — | — |
| 2000-8 | 9.76 | 14.86 | −0.007 | — | — |
| 2000-9 | 9.6 | 14.61 | −0.009 | — | — |
| 2000-10 | 9.78 | 15.09 | 0.006 | — | — |
| 2000-11 | 9.76 | 14.94 | −0.016 | — | — |
| 2000-12 | 9.81 | 15.47 | −0.126 | — | — |
| 200-1 | 9.66 | 15.16 | 1.246 | off scale | 6.8475* |
| 200-2 | 9.66 | 16.09 | −0.079 | 0.024 | 0.15432 |
| 200-3 | 9.68 | 15.79 | −0.039 | 0.014 | 0.08554 |
| 200-4 | 9.76 | 16.44 | −0.045 | 0.012 | 0.08016 |
| 200-5 | 9.76 | 14.78 | −0.06 | — | — |
| 200-6 | 9.62 | 15.07 | −0.066 | — | — |
| 200-7 | 9.61 | 14.75 | −0.083 | — | — |
| 200-8 | 9.72 | 14.93 | −0.04 | — | — |
| 200-9 | 9.78 | 14.81 | −0.073 | — | — |
| 200-10 | 9.6 | 14.81 | −0.104 | — | — |
| 200-11 | 9.75 | 16.24 | −0.072 | — | — |
| 200-12 | 9.81 | 17.65 | −0.078 | — | — |
| bb-1 | 9.82 | 15.9 | −0.039 | 0.044 | 0.26752 |
| bb-2 | 9.75 | 15.34 | 0.014 | 0.002 | 0.01118 |
| bb-3 | 9.91 | 15.32 | −0.054 | 0.002 | 0.01082 |
| bb-4 | 9.87 | 14.83 | −0.025 | — | — |
| bb-5 | 9.68 | 16.08 | −0.032 | — | — |
| bb-6 | 9.77 | 14.71 | −0.033 | — | — |
| bb-7 | 9.6 | 15.56 | −0.047 | — | — |
| bb-8 | 9.72 | 16.23 | −0.031 | — | — |
| bb-9 | 9.7 | 14.9 | −0.069 | — | — |
| bb-10 | 9.77 | 15.54 | −0.057 | — | — |
| bb-11 | 9.79 | 15.91 | −0.049 | — | — |
| bb-12 | 9.75 | 16 | −0.046 | — | — |
| con-1 | 9.93 | 16.115 | −0.061 | 0.006 | 0.03711 |
| con-2 | 9.64 | 15.65 | 0.01 | 0.006 | 0.03606 |
| con-3 | 9.9 | 14.98 | −0.018 | — | — |
| con-4 | 9.74 | 14.71 | −0.005 | — | — |
| con-5 | 9.75 | 14.69 | −0.068 | — | — |
| con-6 | 9.77 | 15.44 | −0.03 | — | — |
| con-7 | 9.95 | 15.44 | −0.039 | — | — |
| con-8 | 9.81 | 16.01 | −0.012 | — | — |
| con-9 | 9.73 | 16.35 | −0.031 | — | — |
| con-10 | 9.68 | 15.77 | −0.031 | — | — |
| con-11 | 9.68 | 14.84 | −0.037 | — | — |
| con-12 | 9.7 | 15.45 | −0.051 | — | — |

Pb — Lead
2000 - Sample with red cells and 2000 μg lead added.
200 - Sample with red cells and 200 μg lead added.
AA - Flame Atomic Absorption Results.
Graphite - Graphite Furnace Atomic Absorption results.
* - Data calculated using flame atomic absorption results.
— Not determined or not available
AA values below 0.1 μg/g may be below detection levels of the instrument
bb - Blood Sample with red cells and with no added Pb.
con - Control Sample of neutral salt solution with no red cells or added Pb.
See Table 3 for summary of data.

TABLE 2

Extraction of Pb from Neutral salt solution

| Sample no. | Vial wt (g) | Vial & Sample (g) | Pb (μg/g) AA | Pb (μg/g) graphite | Total Pb in each tube |
|---|---|---|---|---|---|
| 100-1 | 9.8 | 14.67 | 14.6964 | off scale | 71.57148* |
| 100-2 | 9.74 | 15.59 | 0.684 | off scale | 4.0014* |
| 100-3 | 9.72 | 15.05 | 0.039 | 0.053 | 0.28249 |
| 100-4 | 9.63 | 15.18 | 0.08 | 0.035 | 0.19425 |
| 100-5 | 9.69 | 15.54 | 0.33 | — | 0.19305* |
| 100-6 | 9.79 | 15.39 | 0.066 | — | 0.3696* |
| 100-7 | 9.69 | 16.12 | 0.051 | — | 0.32793* |
| 100-8 | 9.72 | 14.81 | 0.023 | — | 0.11707* |
| 100-9 | 9.78 | 16.78 | 0.031 | — | 0.217* |
| 100-10 | 9.62 | 15.88 | 0.054 | — | 0.33804* |
| 100-11 | 9.7 | 15.53 | 0.019 | — | 0.11077* |
| 100-12 | 9.74 | 15.06 | 0.018 | — | 0.09576* |
| 10-1 | 9.65 | 15.95 | 1.224 | off scale | 7.7112* |
| 10-2 | 9.72 | 15.4 | −0.013 | 0.01 | 0.0568 |
| 10-3 | 9.61 | 15.24 | 0.046 | 0.006 | 0.03378 |
| 10-4 | 9.75 | 14.94 | 0.008 | 0.029 | 0.15051 |
| 10-5 | 9.66 | 15.44 | 0.016 | — | — |
| 10-6 | 9.65 | 15.14 | −0.008 | — | — |
| 10-7 | 9.75 | 15.07 | 0.018 | — | — |
| 10-8 | 9.81 | 15.64 | −0.031 | — | — |
| 10-9 | 9.84 | 16.26 | −0.007 | — | — |
| 10-10 | 9.82 | 15.72 | −0.032 | — | — |
| 10-11 | 9.81 | 15.35 | −0.035 | — | — |
| 10-12 | 9.92 | 15.53 | 0.027 | — | — |

Refer to Table 1 for Control.
100 - Sample with no red cells and 100 μg lead added.
10 - Sample with no red cells and 10 μg lead added.
AA - Flame Atomic Absorption Results.
Graphite - Graphite Furnace Atomic Absorption Results.
* - Data calculated using flame atomic absorption results.
— Not determined or not available
AA values below 0.1 μg/g may be below detection levels of the instrument

TABLE 3

Summary of Data in Tables 1 & 2

| Treatment | Initial Pb (μg) | Pb Added (μg) | Detected Pb (μg) |
|---|---|---|---|
| Blood 2000 | 1.3 | 2000 | 25.72708 |
| Blood 200 | 1.3 | 200 | 7.16752 |
| Blood | 1.3 | 0 | 0.28952 |
| Resin 100 | — | 100 | 77.818828 |

TABLE 3-continued

Summary of Data in Tables 1 & 2

| Treatment | Initial Pb (μg) | Pb Added (μg) | Detected Pb (μg) |
|---|---|---|---|
| Resin 10 | — | 10 | 7.95229 |
| Resin Blk | — | 0 | 0.07317 |

— Not determined

As shown in Table 3, the recovery capacity of the chelating resin for lead from a neutral salt solution in the absence of blood is approximately 80%. When 100 μg of lead was added to the neutral salt solution, more than 77 μg of Pb was removed by the resin and eluted from the column. Similarly, nearly 8 μg of lead were recovered from the resin when 10 μg of lead was added to the neutral salt solution containing no red cells. This result indicates that the resin consistently removes a large percentage of the lead present in solution alone.

However, as shown in Table 3, a smaller amount of lead was removed by the resin when 200 μg of exogenous lead was added to a mixture of red cells and neutral salt solution than when 100 μg of exogenous lead was added to a neutral salt solution in the absence of red blood cells. This can be attributed to sorption of a significant portion of the exogenous lead by the red cells in the mixture.

The results in the last column of Tables 1 and 2 show that elution of lead from the column occurs within the first 15 g of eluant. Thus, the column need only be run for a sufficient time to collect the first 15 g of eluant.

As shown in Table 3, this invention is capable of detecting and concentrating low levels of lead in equilibration between red blood cells and solution. The initial concentration of lead in the samples of red cells was 13 μg/L as determined by a method beyond the scope of this invention. (This initial concentration was determined by hemolyzing the red cells with a solution of Triton X-100, adding a 1% solution of nitric acid to precipitate the protein, and measuring the lead by graphite furnace atomic absorption spectrophotometry.) When a 100 ml sample of red blood cells without additional lead was incubated for 25 hours with neutral salt solution and the resin, approximately 0.3 μg or 22% of the initial 1.3 μg of lead was recovered from the sample by the resin.

As shown in Table 2, the amount of lead detected in the first tube of eluant for the red blood cell sample without additional lead (bb-1) was ten times greater than the amount of lead detected in the first tube of eluant for the control (con-1). This indicates that the method of the present invention is capable of extracting lead from a mixture of cells and neutral salt solution when the amount of lead associated with the red cells is less than 0.2 μg/ml. It appears that lead which is sorbed to the red blood cells equilibrates with or is extracted by the neutral salt solution during the 25 hour incubation period. The lead in the salt solution is then removed and concentrated by the resin and is assayed by conventional methods. This demonstrates the feasibility of using this invention not only to determine the level of lead in blood but also to measure the portion of lead that is believed to constitute bioavailable lead in the blood. Bioavailable lead is the lead that is active and free to react with tissue or with protein in the blood.

The results obtained when large amounts of lead are added to the system support this conclusion. As shown in FIG. 1, the amount of lead extracted by the resin increases as the amount of lead added to the red cell sample increases. FIG. 1 also indicates that red blood cells compete with resin for sorption of added lead. The 200 μg and 2000 μg of lead added to the mixture of red cells and neutral salt solution in comparative examples 1 and 2 greatly exceeds the levels found in blood even in cases where the blood donor is suffering from lead toxicity. Thus, the method described in the present application can be used to monitor levels of lead in both normal individuals and those individuals who have accumulated high levels of this metal in their bodies.

Although one embodiment of this invention has been shown and described, various adaptations and modifications can be made without departing from the scope of the invention as defined in the appended claims.

I claim:

1. A method of extracting lead from a blood sample which comprises:
   a. mixing the blood sample with an neutral salt solution;
   b. then incubating the mixture of the blood sample and neutral salt solution, with a chelating resin which is capable of extracting lead:
   c. then eluting the lead from the chelating resin, using an elution solution;
   d. then measuring the amount of lead eluted.

2. The method as recited in claim 1 wherein the blood sample comprises red blood cells.

3. The method as recited in claim 1 wherein the neutral salt solution comprises a nitrate solution.

4. The method as recited in claim 3 wherein the neutral salt solution comprises a 1 mM to 10M nitrate solution.

5. The method as recited in claim 1 wherein the neutral salt solution comprises about 0.5M $Ca(NO_3)_2$.

6. The method as recited in claim 1 wherein the elution solution is an acid.

7. The method as recited in claim 1 wherein the elution solution comprises an 0.1M to a 10.0M acid solution.

8. The method as recited in claim 1 wherein the elution solution is 0.5M $HNO_3$.

9. The method as recited in claim 1 wherein the amount of element eluted is measured by atomic absorption spectrophotometry.

10. A method of extracting lead from a blood sample which comprises:
    a. mixing red blood cells with a salt solution comprising a 0.1M to a 10M $Ca(NO_3)_2$ solution;
    b. then incubating the mixture of red cells and salt solution with a metal chelating resin;
    c. then eluting the lead from the chelating resin with an elution solution comprising $HNO_3$;
    d. then measuring the amount of lead eluted by atomic absorption spectrophotometry.

11. The method as recited in claim 10 wherein the salt solution is about 0.5M $Ca(NO_3)_2$.

12. The method as recited in claim 10 wherein the elution solution is about 0.5M $HNO_3$.

* * * * *

UNITED STATES PATENT AND TRADEMARK OFFICE
CERTIFICATE OF CORRECTION

PATENT NO. : 5,407,831
DATED : April 18, 1995
INVENTOR(S) : Jing

It is certified that error appears in the above-indentified patent and that said Letters Patent is hereby corrected as shown below:

Column 3, line 21, delete "$NAN_3$" and insert --$NaN_3$--.

Column 3, line 32, delete "$NAN_3$" and insert --$NaN_3$--.

Col. 6, line 40
Claim 5, line 2, delete "0.5M" and insert --0.05M--.

Col. 6, line 62
Claim 11, line 2, delete "0.5M" and insert --0.05M--.

Signed and Sealed this

Seventeenth Day of October, 1995

Attest:

BRUCE LEHMAN

Attesting Officer        Commissioner of Patents and Trademarks